(12) United States Patent  
Ablordeppey

(10) Patent No.: US 8,288,410 B2
(45) Date of Patent: *Oct. 16, 2012

(54) 3-SUBSTITUTED QUINOLINIUM AND 7H-INDOLO[2,3-C]QUINOLINIUM SALTS AS NEW ANTIINFECTIVES

(75) Inventor: Seth Y. Ablordeppey, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 1134 days.

This patent is subject to a terminal disclaimer.

(21) Appl. No.: 12/169,165

(22) Filed: Jul. 8, 2008

(65) Prior Publication Data

US 2012/0165369 A1 Jun. 28, 2012

(51) Int. Cl.
*A01N 43/42* (2006.01)
*A01N 33/12* (2006.01)
*A61K 31/47* (2006.01)
*A61K 31/14* (2006.01)
*C07D 215/00* (2006.01)
*C07D 215/38* (2006.01)
*C07C 211/00* (2006.01)

(52) U.S. Cl. ........ 514/312; 514/313; 514/643; 546/153; 546/159; 564/282

(58) Field of Classification Search .................. 514/311, 514/643, 312, 313; 546/152, 153, 159; 564/282
See application file for complete search history.

(56) References Cited

U.S. PATENT DOCUMENTS 5,925,647 A 7/1999 Bierer

OTHER PUBLICATIONS

Gaillard et. al., Synlett, 2005, Georg Thieme Verlag Stuttgart, vol. 3, pp. 441-444.*
van den Berg et. al., Journal of Organic Chemistry, 2006, American Chemical Society, vol. 71, pp. 2666-2676.*
Miyoshi et. al., The Journal of Biological Chemistry, 1997, The American Society for Biochemistry and Molecular Biology, vol. 272, issue 26, pp. 16176-16183.*
Owen et. al., Biochemistry Journal, 2000, Biochemical Society, vol. 348, pp. 607-614.*
Mardenborough, L.G. et al.: Identification od bis-quindolines as new antiinfective agents. Bioorg. & Medicin. Chem., vol. 13, pp. 3955-3963, 2005.
Muhammad, I.; Dunbar, D. C.; Khan, S. I.; Tekwani, B. L.; Bedir, E.; Takamatsu, S.; Ferreira, D, Walker LA., J Nat Prod. 2003, 66, 962-7].
Ablordeppey, S. Y.; Hufford, C. D.; Borne, R. F.; Dwuma-Badu, D. Planta Med. 1990, 56, 416.
Cimanga K.; De Bruyne T.; Lasure A; Van Poel, B.; Pieters, L.; Claeys, M.; Vanden Berghe, D.; Kambu, K.; Tona, L.; Vlietinck, A I. Planta Medica, 1996, 62,22-27.
Ablordeppey, S. Y.; Fan, P.; Ablordeppey, I. H.; Mardenborough, L. Curr Med. Chem. 1999, 6, 1151-1195].
Oyekan, A O.; Ablordeppey, S. Y Gen. Pharmacol. 1993, 24, 1285-1290.
Oyekan, A O.; Ablordeppey, S. Y Gen. Pharmacol., 1993, 24, 461-469.
Oyekan AO.; Ablordeppey S. Y Med. Chem. Res. 1996, 6, 602-610.
Singh, M.; Singh, M. P.; Ablordeppey, S. Drug Dev Ind Pharm 1996, 22,377-381].
Muhammad, I.; Bedir, E.; Khan, S. I.; Tekwani, B. L.; Khan, I. A.; Takamatsu, S.; Pelletier, I.; Walker, L. A. J Nat Prod. 2004, 67, 772-7.
Bierer D. E.; Fort D. M.; Mendez C. D.; Luo I.; Imbach P. A; Dubenko L. G.; Jolad S. D.; Gerber, R. E.; Litvak, I.; Lu Q.; Zhang P.; Reed M. I.; Waldeck N.; Bruening R. C.; Noamesi B. K.; Hector R. F.; Carlson T. J.; King S. R. J Med Chem. 1998,41,894-901.
Boakye-Yiadom, K.; Heman-Ackah, S. M. J Pharm Sci 1979, 68,1510-1514.
Sawer, I. K.; Berry M. I.; Brown M. W.; Ford, J. L. J Applied Bacteriol, 1995, 79,314-321.
Dassonneville, L.; Lansiaux, A; Wattelet, A; Wattez, N.; Mahieu, C.; Van Miert, S.; Pieters L.; Bailly, C. Eur J Pharmacol2000, 409, 9-18.
Franzblau et al [1998. J Clin Microbiol, 36, 362-366].

(Continued)

*Primary Examiner* — Sreeni Padmanabhan
*Assistant Examiner* — Sarah Pihonak
(74) *Attorney, Agent, or Firm* — Parks IP Law LLC; Collen A. Beard

(57) ABSTRACT

The present invention relates to quinolinium antiinfective agents in which the qunolinium nucleus is fused to an indole ring or the qunolinium nucleus is linked to a cyclic structure through an opened indole or a benzothiophene or benzofuran ring. The compound is further substituted with various substituent groups.

The compounds are represented by formula (I), (II) and (III):

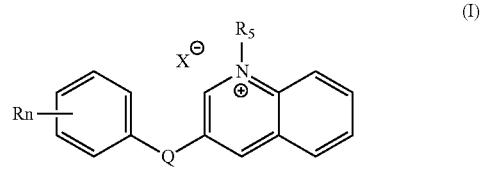

(I)

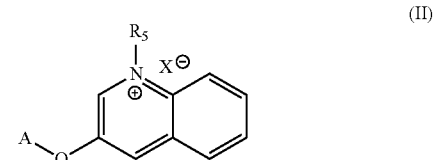

(II)

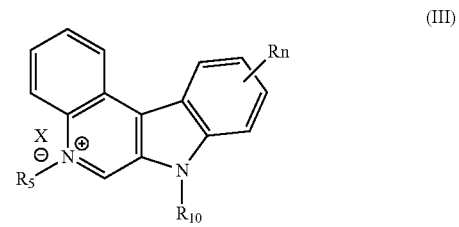

(III)

Pharmaceutical compositions and methods of use are also included.

7 Claims, No Drawings

OTHER PUBLICATIONS

Wright, C. W.; Phillipson, J. D.; Awe, S. 0.; Kirby, G. c.; Warhurst, D. C.; Quetin-Leclercq, J.; Angenot, L. Phytother Res 1996, 10, 361-363.

Grellier, P.; Ramiaramanana, L.; Millerioux, V.; Deharo, E.; Schrevel, J.; Frappier, F.; Trigalo, F.; Bodo, B.; Pousset, J.-L. Phytother Res, 1996, 10 317-321.

Kirby, G. C.; Paine, A; Warhurst, D. C.; Noamesi, B. K; Phillipson, J. D. Phytother Res, 1995, 9,359-63.

Guoyi, M.; Khan, S.; Jacob, M. R; Tekwani, B. L.; Li, Z.; Pasco, D. S.; Walker, L. A.; Khan, I. A.; Antimicrob Agents Chemother, 2004, 48, 4450-4452.

Dassonneville L.; Bonjean K; De Pauw-Gillet, M.-C.; Colson P.; Houssier, C.; QuetinLeclercq, I; Angenot, L.; Bailly, C. Biochemistry, 1999, 38, 7719-26.

Bailly, C.; Laine, W.; Baldeyrou, B.; De Pauw-Gillet, M.-C.; Colson, P.; Houssier, C.; Cimanga, K; Van Miert, S.; Vlietinck, AJ.; Pieters, L. Anticancer Drug Des, 2000, 15, 191-201.

Bonj ean, K.; De PauwGillet, M.-C.; Defresne, P.; Colson P.; Houssier, c.; Dassonneville L.; Bailly, C.; Greimers, R.; Wright, c.; Quetin-Leclercq, J.; Tits, M.; Angenot, L. Biochemistry, 1998, 37, 5236-5146.

Guyen, B.; Schultes, C. M; Hazel, P.; Mann, J.; Neidle, S.Org Biomol Chem, 2004, 2, 981-8.

Ablordeppey, S.Y.; Fan, P.; Clark, A. M.; Nimrod, A Bioorg Med Chem, 1999, 7, 343-349.

Mardenborough L. G.; Fan, P. c.; Ablordeppey, S. Y.; Nimrod, A; Clark A M. Med Chem Res, 1999,9, 118-132.

Ablordeppey, S.Y.; Fan, P.; Li, S.; Clark, A M.; Hufford, C. D. Bioorg Med Chem, 2002, 10,1337-1346.

Holt, S. J.; Petrow, V. .J Chem. Soc. 1947,607-611.

Cooper, M. M.; Lovell, I. M.; Joule, J. A. Tetrahedron Leu, 1996,37,4283-4286.

Radl, S; Konvicka, P.; Vachal, P. J Heterocycl Chem, 2000, 37, 855-862.

Yang, S.-W.; Abdel-Kader, M.; Malone, S.; Werkhoven, M. C. M.; Wisse, J. H.; Bursuker, I.; Neddermann, K; Fairchild, C.; Raventos-Suarez, C.; Menendez, AT.; Lane, K.; Kingston, D. G. I. J Nat Prod, 1999, 62, 976-983.

Bierer D. E.; Dubenko L. G.; Zhang P.; Lu Q.; Imbach P. A; Garofalo A W.; Phuan P. -W.; Fort D. M.; Litvak J.; Gerber R. E.; Sloan B.; Luo J.; Cooper R.; Reaven G. M. J Med Chem 1998, 41, 2754-2764.

Chen, J. J.; Deady, L. W.; Desneves, 1.; Kaye, A. J.; Finlay, G. J.; Baguley, B. C.; Denny, W. A. Bioorg Med Chem, 2000, 8,2461-2466.

Zhu, Xue Y.; Mardenborough, Leroy G.; Li, Shouming; Khan, Abdul; Zhang, Wang; Fan, Pincheng; Jacob, Melissa; Khan, Shabana; Walker, Larry and Ablordeppey, Seth, Bioorg Med Chem, 2007, 15,686-695.

* cited by examiner

3-SUBSTITUTED QUINOLINIUM AND 7H-INDOLO[2,3-C]QUINOLINIUM SALTS AS NEW ANTIINFECTIVES

GOVERNMENT SUPPORT

This research was supported by grants from the National Institutes of Health grant numbers NIH/NCRR/RCMI G12RR03020, and NIH/NCRR/HHS1 C06 RR012512-01.

FIELD OF THE INVENTION

The present invention pertains to 3-substituted quinolinium and 7H-indolo[2,3,-c]quinolinium antiinfective compounds and pharmaceutically acceptable salts, compositions, and methods of treatment.

BACKGROUND OF THE INVENTION

Infections caused by *Staphylococcus aureus*, methicillin resistant *Staphylococcus aureus* (MRSA) and related gram positive pathogens are growing and continuous medical concern. Vancomycin and other glycopeptide antibiotics, are currently the agents of choice for combating these infections which are predominantly encountered in hospital settings. With the increased usage of Vancomycin, resistant strains have been found and are referred to as vancomycin intermediate-resistant *Staphylococcus aureus* (VISA). Schito, G. C., *The Importance of the Development of Antibiotic Resistance in Staphylococcus Aureus*, Clin. Microbiol. Infect., 2006, 12 Suppl. 1:3-8. Additionally, there is currently an epidemic of community-acquired MRSA (CA-MRSA) pneumonia in this country, which is reportedly linked to *Staphylococcus aureus* (SA) infection. Hageman, J. C., et al., *Severe Community-Acquired Pneumonia Due to Staphyloccus aureus*, 2003-04 Influenza Season, Emerg. Infect. Dis. 2006, available at the Centers for Disease Control website. Consequently, there is a dire need to develop new structural entities with a new mode of action against MSRA, other nosocomial and CA-MRSA opportunistic infections.

Furthermore, infections caused by opportunistic pathogens such as *Cryptococcus neoformans* (Cn or *C. neoformans*), *Candida albicans* (Ca or *C. albicans*), *Aspergillus fumigatus* (Af or *A. fumigatus*) are growing medical concerns for immunucompromised patients such as those with AIDS. If not properly treated, these mycotic infections are often fatal. Despite tremendous progress in the development of new antifungal agents, drugs currently on the market including Amphotericin B in combination with Flucytosine and azoles present serious limitations. Echinocandins, the newest antifungal agents are fungistatic against clinically relevant *Aspergillus* species and are resistant in vitro to *Cryptococcus* and Zygomycetes. Thus, with the rising incidence of systemic mycoses due to immunosuppresion and neutropenia, there is an urgent need to develop novel systemic antifungal drugs.

It has been reported that cryptolepine and other alkyl substituted indolo[3,2-b]quinolines, also referred to as quindolines constitutes an important structural moiety in the literature because it possesses antiinfective activity against some opportunistic infectious organisms. Etukala, J. R.; Suresh Kumar, E. V. K.; Ablordeppey, S. Y., *A Short and Convenient Synthesis and Evaluation of the Antiinfective Properties of Indoloquinoline Alkaloids: 10H indolo[3,2-b]quinoline and 7H-indolo[2,3-c]quinolines*. J. Heterocycl Chem., 2008, 45, 507-511, Ablordeppey S. Y.; Fan, P.; Li, S.; Clark, A. M.; Hufford, C. D, *Substituted Indoloquinolines as New Antifungal Agents*, Bioorganic and Medicinal Chemistry, 2002, 10, 1337-1346. Zhu, et al., *Synthesis and Evaluation of Isosteres of N-Methyl indolo[3,2-b]-quinoline (cryptolepine) as New Antiinfective Agents*, Bioorg. Med. Chem., 2007, 15, 686-695. However, the action of these compounds appears to operate through intercalation to DNA. Bonjean, K., et al., *The DNA Intercalating Alkaloid Cryptolepine Interferes With Topoisomerase II and Inhibits Primarily DNA Synthesis in B16 Melanoma Cell*, Biochemistry, 1998, 37, 5236-5146. PCT/US2007/007976 referenced various publications showing that alkylation of nitrogen at the 5-position with omega-phenylpentyl and omega-cyclohexylpentyl groups produced high antifungal potency and broadened the spectrum of activities.

The present invention relates to novel 3-substituted quinolinium and 7H-indolo[2,3-c]quinolinium antiinfective compounds, which are ring-opened and angular quindoline analogs/isosteres that are capable of entering the cells and more importantly in crossing the blood-brain barrier to elicit antiinfective actions. These novel 3-substituted quinolinium antiinfectives have been shown to be more potent, yet less toxic than the parent tetracyclic quindoline. The angular quindolinium compounds have been shown to have better anti-MRSA, anti-cryptococcal and cytoxicity profiles than those of the linear quindolinium salts represented by cryptolepine. The antiinfectives of the present invention thus comprise an important contribution to therapy for treating infections caused by difficult to control pathogens. There is an increasing need for agents effective against pathogens such as MRSA, *C. neoformans*, and other fungal pathogens and protozoa which are at the same time relatively free from undesirable side effects.

BRIEF SUMMARY OF THE INVENTION

In accordance with the purpose(s) of this invention, as embodied and broadly described herein, this invention in one aspect, relates to quinolinium antiinfectives for—MRSA and anti-opportunistic pathogens. The 3-substitued and 7H-indolo[2,3-c]quinolinium compounds impart MRSA and Cryptococcal activity with less concerns associated with current glycopeptide antibiotics and antifungal treatments.

In another aspect, this invention relates to a compound having the formula (I):

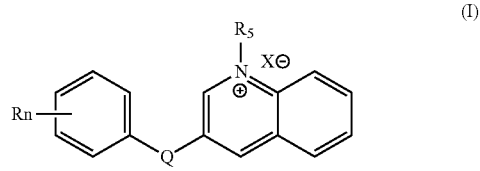

or a pharmaceutically acceptable salt thereof, wherein:

Rn is an electron withdrawing or electron donating group, and n is the position of substitution of R;

$R_5$ is a straight or branched 1-5 carbon or heteroatom chain, which is unsubstituted or substituted terminally by a cycloalkyl or aromatic ring, which is unsubstituted or substituted, or a cycloalkyl or aromatic ring, or a heteroaromatic ring, or other structural isomer or complex thereof; and Q is NH, N—$CH_3$, N—$R_5$, S, SO and O In yet another aspect this invention relates to a compound of formula (II):

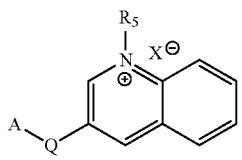

(II)

or a pharmaceutically acceptable salt thereof, wherein:

$R_5$ may be the same or different and is a straight or branched 1-5 carbon or heteroatom chain, which is unsubstituted or substituted terminally by a cycloalkyl or aromatic ring, which is unsubstituted or substituted, or a heteroaromatic ring, or other structural isomer or complex thereof;

Q is NH, N—$CH_3$, N—$R_5$, S, SO or O; and

A is a cycloalkyl or heterocyclic system, which is unsubstituted or substituted with electron donating or electron withdrawing groups.

In another aspect this invention relates to a compound of formula (III):

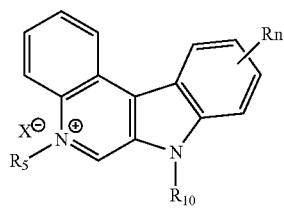

(III)

or a pharmaceutically acceptable salt thereof, wherein:

$R_n$ is an electron withdrawing or electron donating group, and n is the position of substitution on R and;

$R_5$ and $R_{10}$ may be the same or different and are a straight or branched 1-5 carbon or heteroatom chain, which is unsubstituted or substituted terminally by a cycloalkyl or aromatic ring, which is unsubstituted or substituted, or a cycloalkyl or aromatic ring, or a heteroaromatic ring or other structural isomer or complex thereof.

Pharmaceutical compositions, methods of treatment and an article of manufacture are also included herein.

DETAILED DESCRIPTION OF THE INVENTION

The invention is described herein in detail using the terms defined below unless otherwise specified.

It must be noted that as used in the specification and the appended claims, the singular forms "a" "an" and "the" include plural referents unless the context clearly dictates otherwise. Thus, for example, reference to "a cyclic compound" includes mixtures of aromatic compounds.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

The term "alkyl" refers to a monovalent alkane (hydrocarbon) derived radical from 1 to 10 carbon atoms unless otherwise defined. It may be straight, branched or heteroatom chain, or cyclic. Preferred alkyl groups are methyl, ethyl, propyl, isopropyl, butyl, t-butyl, pentyl and the like. When substituted, alkyl groups may be substituted terminally by a cycloalkyl or aromatic ring, or other structural isomer or complex, including omega-phenylpentyl and omega-cyclohexyl pentyl moieties.

Cycloalkyl is a specie of the alkyl containing from 3 to 15 carbon atoms without alternating or resonating double bonds between carbon atoms. It may contain from 1 to 4 rings which are fused.

Aromatic ring or "aryl" includes for example phenyl, substituted phenyl and the like, as well as rings that are fused, e.g. naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms.

The term "quaternary nitrogen" and "positive charge" refer to tetravalent, positively charged nitrogen atoms including, e.g., the positive charged nitrogen in a tetraalkylammonium group (e.g., tetramethylammonium), heteroarylium (e.g., N-methyl pyridinium), basic nitrogens which are protonated at physiological pH and the like. Cationic groups thus encompass positively charged nitrogen-containing groups, as well as basic nitrogen-containing groups which are protonated at physiologic pH.

The term "quaternary amine" defines the pharmaceutically acceptable quaternary ammonium salts which the antiinfective compounds of the instant invention are able to form by reaction between a basic nitrogen of a compound of formula (I), ((II) or (III) and an appropriate quaternizing agent, such as, for example, an optionally substituted alkylhalide, arylhalide or arylalkylhalide, e.g. alkyliodide or benzyliodide. A quaternary amine has a positively charged nitrogen. Pharmaceutically acceptable counterions include chloro, bromo, iodo, trifluoromethanesulfonate (triflate) and tosylate.

Other salts encompassed within the term "pharmaceutically acceptable salts" refer to non-toxic salts of the compounds of this invention which are derived from organic or inorganic acids. Representative salts include the following salts: acetate, adipate, alginate, aspartate, benzenesulfonate, benzoate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrocloride, hydrobromide, hydroiodide, 2-hydroxyethanesulfonate, lactate, maleate, methanesulfonate, 2-naphthlenesulfonate, nicotinate, oxalate, pamoate, pectinate, persulfate, 3-phenylpropionate, picrate, pivalate, propionate, succinate, tartrate, thiocyanate, tosylate, and undecanoate.

The term "heteroatom" means O, S or N selected on an independent basis.

Halogen and "halo" refer to bromine, chlorine, fluorine and iodine.

When a group is termed "substituted", unless otherwise indicated, this means that the group contains 1 to 4 substituents thereon.

The quinolinium compounds of the present invention are useful per se and in their pharmaceutically acceptable salt forms for the treatment of bacterial, fungal and protozoan infections in humans and animal subjects. The term "pharmaceutically acceptable ester, salt or hydrate," refers to those salts, and hydrated forms of the compounds of the present invention which would be apparent to the pharmaceutical chemist, i.e., those which are substantially non-toxic and which may favorably affect the pharmacokinetic properties of said compounds, such as palatability, absorption, distribution, metabolism and excretion. Other factors, more practical in nature, which are also important in the selection are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is concerned with pharmaceutical compositions and methods for treating bacterial, fungal and protozoan infections utilizing as an active ingredient the novel quinolinium compounds.

X represents a pharmaceutical acceptable counterion to maintain the appropriate charge balance. Most anions derived from inorganic or organic acids are suitable. Representative examples of such counterions are the following: acetate, adipate, aminosalicylate, anhydromethylenecitrate, ascorbate, aspartate, benzoate, benzenesulfonate, iodide, bromide, chloride, fluoride, citrate, camphorate, camphorsulfonate, estolate, ethanesulfonate, fumarate, glucoheptanoate, gluconate, glutamate, lactobionate, malate, maleate, mandelate, methanesulfonate, nitrate, pantothenate, pectinate, phosphate/diphosphate, polygalacturonate, propionate, salicylate, stearate, succinate, sulfate, tartrate, tosylate, triflate, and trifluoromethanesulfonate. Other suitable anionic species will be apparent to the ordinary skilled chemist.

The compounds of the present invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injections, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the compound selected, the virulence of the infection and other factors. Such matters, however, are left to the routine discretion of the physician according to principals of treatment well known in the antiinfective arts. Another factor influencing the precise dosage regimen, apart from the nature of the infection and peculiar identity of the individual being treated, is the molecular weight of the compound.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Using standard susceptibility tests, the compounds of the invention were determined to be active against MRSA, *C. neoformans* and several other bacteria, fungi and protozoa. More specifically, the antibacterial and antifungal testing was carried out in the following manner. *Cryptococcus neoformans* ATCC 90113 and MRSA were obtained from the American Type Culture Collection (Manassas. Va.). Several others including *Candida albicans* ATTC 90028, *Aspergillus fumigatus* ATCC 90906 and *Mycobacterium intracellulare* (*M. intracellulare*) ATCC 23086 were also procured. Susceptibility testing was performed using a modified version of the National Committee for Clinical Laboratory Standards method. *M. intracellulare* was tested using a modified method of Franzblau, et al., J. Clin. Microbiol., 1998, 36, 362-366. DMSO solutions of samples were serially diluted in saline, and transferred in duplicate to 96 well microplates. Microbial suspensions were diluted in the broth to afford desired colony forming units/mL according to the 0.5 McFarland Standard [*C. Albicans*: either Saboraud Dextrose broth (SDB) or RPMI 1640, *C. neoformans*: SDB, *A fumigatus*: either YM broth (for MICS) or RPMI-1640+5% Alamar Blue.] After adding microbial cultures to the sampled afforded a final volume of 200 μL and final test concentration starting with 20 μg/mL, plates were read prior to and after final incubation using either fluorescence at 544ex/590em (*M intracellulare, A. fumigatus*) using the Polarstar galaxy reader (Biotek Instruments, Vermont). Growth (saline only), solvent and blank (media only) controls were included on each test plate. Drug controls [Ciprofloxacin (ICN Biomedicals, Ohio) for bacteria and Amphotericin B (ICN Biomedicals, Ohio) for fungi] were included in each assay. Percent growth was calculated and plotted versus test concentration to afford $IC_{50}$ (sample concentration that affords 50% inhibition or growth of the organism). The minimum inhibitory concentration (MIC) was determined by visually inspecting the plate, and is defined as the lowest test concentration that allows no detectable growth (for Almar Blue assays, no color change from blue to pink).

The biological activities of the compounds of the invention were evaluated and the results are shown below in Tables 1, 2 and 3.

TABLE 1

Physicochemical Data and Antifungal/Anti-MRSA Activities (in μg/mL) of Synthetic Compounds

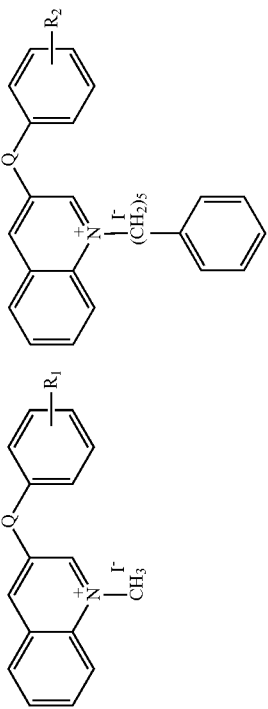

| Comp | R₁ | R₂ | Q | % Yield[b] | MP °C[c] | Ca IC₅₀ | Ca MIC | Ca MFC | Cn IC₅₀ | Cn MIC | Cn MFC | A fu IC₅₀ | A fu MIC | A fu MFC | MRS IC₅₀ | MRS MIC | MRS MFC | TC₅₀ Vero Cells |
|---|---|---|---|---|---|---|---|---|---|---|---|---|---|---|---|---|---|---|
| XYZ-III-53 | H | H | S | 81 | 145-146 | 5.5 | 10 | — | 15 | 5.0 | 10 | 1.3 | — | — | 1.0 | 2.5 | 10 | |
| XYZ-III-54 | 4-F | H | S | 75 | 166-167 | — | — | — | — | — | — | — | — | — | — | — | — | |
| XYZ-III-62 | 4-CF₃ | H | S | 78 | 174-175 | 20 | — | — | 7.0 | — | — | — | — | — | 5.5 | 10 | — | NC |
| XYZ-III-63 | | 4-F | S | 85 | 159-160 | — | — | — | — | — | — | — | — | — | — | — | — | |
| XYZ-III-65 | 4-OMe | 4-CF₃ | S | 78 | 148-150 | 5.5 | 10 | — | 2.0 | 5.0 | 10 | 3.0 | 5.0 | — | 2.0 | 5.0 | 10 | |
| XYZ-III-66 | 4-OMe | 4-CF₃ | S | 74 | 129-130 | — | — | — | — | — | — | — | — | — | 1.0 | 2.5 | 10 | |
| XYZ-III-71 | | 4-OMe | S | 87 | 179-180 | — | — | — | — | — | — | — | — | — | — | — | — | |
| XYZ-III-72 | | 4-OMe | S | 72 | 172-173 | — | — | — | 9.5 | 20 | 10 | 3.5 | 10 | — | 2.0 | 5.0 | 10 | |
| XYZ-III-74 | | 2-Cl | S | 68 | 125-126 | — | — | — | 2.0 | 5.0 | 20 | 0.70 | 2.5 | — | 1.0 | 2.5 | 10 | |
| XYZ-III-83 | | H | O | 79 | 164-165 | — | — | — | — | — | — | 2.0 | — | — | 15 | 20 | 10 | |
| XYZ-III-85 | | 2-Br | S | 78 | 141-142 | 20 | — | — | 1.5 | 5.0 | 10 | 0.50 | 5.0 | — | 0.95 | 2.5 | 10 | |
| XYZ-III-87 | | 3-Br | S | 80 | 172-173 | — | — | — | 2.0 | 5.0 | 20 | 3.0 | 10 | — | 2.0 | 5.0 | 20 | |
| XYZ-III-89 | | 4-Br | S | 86 | 181-182 | 15 | — | — | 1.0 | 2.5 | 10 | 1.5 | 2.5 | — | 1.5 | 2.5 | 10 | |
| XYZ-IV-18 | | 2-OMe | S | 82 | 142-143 | 3.0 | 10 | — | 0.85 | 0.63 | 5.0 | 0.09 | 1.3 | 10 | 0.25 | 0.63 | 5.0 | |
| XYZ-IV-19 | | 2-F | S | 74 | 172-173 | 2.5 | 10 | — | 0.25 | 2.5 | 2.5 | 0.20 | 0.31 | — | 0.40 | 0.63 | 5.0 | |
| XYZ-IV-20 | | 3-OMe | S | 80 | 168-169 | 7.0 | 20 | — | 1.5 | 2.5 | 10 | 0.55 | 1.3 | — | 0.70 | 1.3 | 10 | |
| XYZ-IV-21 | | 3-F | S | 78 | 144-145 | 3.0 | 10 | — | 0.40 | 0.63 | 2.5 | 0.10 | 0.16 | — | 0.20 | 0.16 | 20 | |
| XYZ-IV-25 | | 2-CF₃ | S | 87 | 182-183 | 0.4 | 1.3 | 20 | 0.06 | 0.16 | 0.63 | 0.03 | 0.08 | 10 | 0.05 | 0.16 | 2.5 | |
| XYZ-IV-54 | | 3-CF₃ | S | 81 | 186-188 | 6.0 | 10 | 2.5 | 1.5 | 2.5 | 20 | 1.5 | 5.0 | — | 0.85 | 2.5 | 10 | |
| XYZ-IV-58 | | 3,5-(CF₃)₂ | S | 87 | 194-196 | ND | — | — | ND | — | — | ND | — | — | ND | — | — | NC |
| XYZ-IV-79 | | H | SO | 86 | 192-193 | — | — | — | 15 | — | — | — | — | — | 1.5 | 5.0 | — | |
| XYZ-IV-84 | | 4-F | SO | 81 | 184-185 | — | — | — | 15 | 20 | — | — | — | — | 0.80 | 5.0 | 20 | |
| XYZ-IV-87 | | 3-CF₃ | SO | 83 | 176-177 | — | — | — | 6.5 | 20 | 20 | — | — | — | 0.25 | 1.3 | 10 | |
| XYZ-IV-90 | | 2-CF₃ | SO | 82 | 184-186 | 15 | — | — | 5.5 | 20 | — | 15 | — | — | 0.25 | 0.63 | 20 | |
| XYZ-IV-98 | | 2-F | SO | 78 | 194-195 | — | — | — | 5.5 | 5.0 | — | — | — | — | 0.35 | 1.3 | 10 | |
| XYZ-IV-100 | | 2-Cl | SO | 76 | 187-188 | — | — | — | 15 | 20 | — | — | — | — | 1.5 | 5.0 | — | |
| XYZ-V-9 | | 3,5-(CF₃)₂ | SO | 76 | 191-192 | — | — | — | 10 | 5.0 | 10 | — | — | — | 0.75 | 2.5 | 10 | |
| XYZ-V-13 | | 4-Br | SO | 78 | 166-167 | 10 | 20 | — | 3.0 | 20 | 20 | — | — | — | 0.20 | 0.63 | — | |
| XYZ-V-20 | | 4-OMe | SO | 77 | 203-204 | — | — | — | 7.0 | 10 | — | — | — | — | 0.50 | 2.5 | — | |
| XYZ-V-21 | | 4-OMe | SO | 52 | 200-201 | — | — | — | — | — | — | — | — | — | 7.00 | 20 | — | |
| XYZ-V-23 | | 3-OMe | SO | 45 | 158-160 | 15 | — | — | 15 | — | — | — | — | — | 2.50 | 10 | — | |

TABLE 1-continued

Physicochemical Data and Antifungal/Anti-MRSA Activities (in μg/mL) of Synthetic Compounds

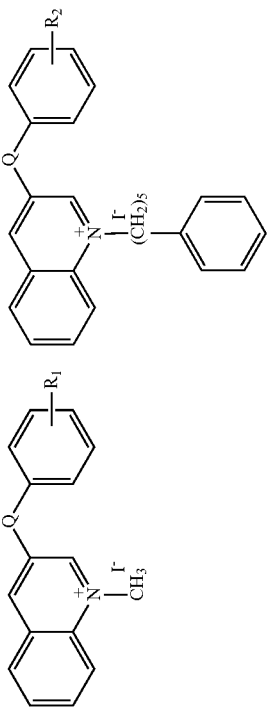

| Comp | R₁ | R₂ | Q | % Yield[b] | MP °C[c] | Ca IC₅₀ | Ca MIC | Ca MFC | Cn IC₅₀ | Cn MIC | Cn MFC | A fu IC₅₀ | A fu MIC | A fu MFC | MRS IC₅₀ | MRS MIC | MRS MFC | TC₅₀ Vero Cells |
|---|---|---|---|---|---|---|---|---|---|---|---|---|---|---|---|---|---|---|
| XYZ-V-27 | | 4-CF₃ | SO | 81 | 189-190 | — | — | — | 6.0 | 10 | 20 | — | — | — | 0.50 | 1.3 | — | |
| XYZ-V-29 | | 3-Br | SO | 79 | 173-174 | — | — | — | 5.5 | 10 | 20 | — | — | — | 0.90 | 2.5 | — | NC |
| XYZ-IV-45 | | | | 74 | 175-176 | — | — | — | 0.60 | 2.5 | 20 | 9.0 | 20 | — | 0.95 | 5.0 | — | NC |
| XYZ-IV-52 | | | | 45 | 154-156 | — | — | — | 4.0 | 10.0 | — | 5.0 | 10 | — | 2.0 | 5.0 | — | NC |
| XYZ-IV-55 | | | | 64 | 167-168 | 15 | — | — | 0.95 | 2.5 | 20 | 7.5 | — | — | 0.80 | 2.5 | 10 | |
| XYZ-IV-59 | | | | 54 | 206-208 | | | | | | | | | | | | | |
| XYZ-IV-51 | | | | 83 | 158-160 | 6.5 | — | — | 1.5 | 2.5 | 20 | 0.90 | 2.5 | — | 0.85 | 2.5 | 20 | NC |
| XYZ-VI-15 | | 2-CN | S | 69 | 174-175 | ND | — | — | ND | 5.0 | 10 | ND | 20 | — | ND | 3.1 | — | |
| XYZ-V-62 | | 4-Cl | CO | 81 | 160-161 | 7.0 | 10 | — | 2.0 | 2.5 | 10 | 10 | 20 | — | 0.20 | | — | |
| Amph B | | | | | | 0.25 | 0.63 | 1.3 | 0.85 | 2.5 | 2.5 | 0.90 | 2.5 | 2.5 | ND | | — | 6.5 |

Abbreviations: Ca = Candida albicans; Cn = Cryptococcus neoformans; Af = Aspergillus fumigatus; Amph B = Amphotericin B; NC = Not toxic at 10 μg/mL; Cp = Cyclohexypentyl; (-) = >20 μg/mL.
[a]Recrystallization solvents are A = MeOH, B = MeOH—CH₂Cl₂, C = MeOH—Et₂O, D = MeOH—EtOAc
[b]Yields were not optimized.
[c]Melting points were uncorrected.
[d]All compounds were subjected to CHN analysis and each passed within 0.4% of the theoretical value.

TABLE 1-continued
Physicochemical Data and Antifungal/Anti-MRSA Activities (in μg/mL) of Synthetic Compounds

TABLE 2

Physicochemical Data and Antifungal/Anti-MRSA Activities (in μg/mL) of Synthetic Compounds

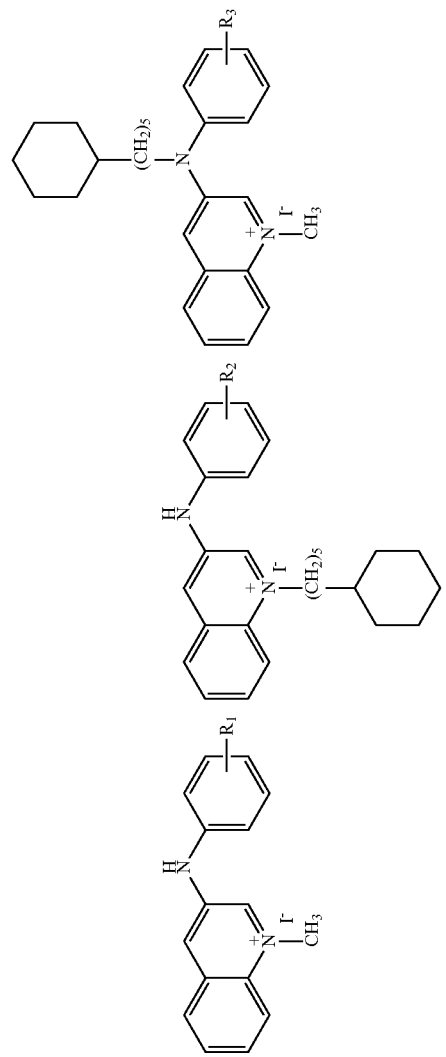

| Comp | R₁ | R₂ | R₃ | MP °C[c] | Ca IC$_{50}$ | Ca MIC | Ca MFC | Cn IC$_{50}$ | Cn MIC | Cn MFC | Af IC$_{50}$ | Af MIC | Af MFC | MRSA IC$_{50}$ | MRSA MIC | MRSA MFC | TC$_{50}$ Vero Cells |
|---|---|---|---|---|---|---|---|---|---|---|---|---|---|---|---|---|---|
| JRE-3-20-1 | | | 4-CF₃ | 154-156 | 0.65 | 1.6 | 3.1 | 0.65 | 1.6 | 3.1 | 1.0 | 3.1 | 6.3 | 0.40 | 0.78 | 1.6 | 25 |
| JRE-3-61-1 | | | 3-CF₃ | 111-112 | 1.0 | 2.5 | 2.5 | 0.85 | 1.3 | 2.5 | 1.5 | 2.5 | 10 | 0.45 | 0.63 | 1.3 | >10 |
| JRE-4-9-1 | | | 4-Cl | 176-177 | 0.45 | 1.3 | 5.0 | 0.40 | 0.63 | 2.5 | 0.80 | 1.3 | 10 | 0.40 | 0.63 | 0.63 | 10 |
| JRE-4-3-1 | | | 3-Cl | 85-87 | 0.90 | 2.5 | 10 | 0.85 | 1.3 | 5.0 | 1.0 | 2.5 | 25 | 0.80 | 1.3 | 2.5 | >10 |
| JRE-3-19-1 | | | H | 156-158 | 1.0 | 3.1 | 13 | 0.55 | 0.78 | 6.3 | 0.80 | 1.6 | 10 | 0.85 | 1.6 | 6.3 | |
| JRE-3-68-1 | | | 4-OMe | 181-183 | 0.80 | 1.3 | 1.3 | 0.50 | 1.3 | 5.0 | 0.85 | 1.3 | 10 | 0.50 | 1.3 | 1.3 | >10 |
| JRE-3-69-1 | | | 3-OMe | 165-167 | 0.85 | 2.5 | 2.5 | 0.55 | 1.3 | 5.0 | 0.70 | 1.3 | 10 | 0.50 | 1.3 | 1.3 | >10 |
| JRE-3-99-1 | | | 4-OCF₃ | 161-163 | 0.45 | 1.3 | 10 | 0.70 | 1.3 | 1.3 | 0.95 | 2.5 | 2.5 | 0.65 | 1.3 | 1.3 | >10 |
| JRE-2-81-1 | 3-Cl | | | 211-213 | — | — | — | — | — | — | — | — | — | — | — | — | |
| JRE-2-42-1 | 2-Cl | | | 208-210 | — | — | — | — | — | — | — | — | — | — | — | — | |
| JRE-3-45-1 | | 4-OMe | | 135-136 | 2.0 | 25 | — | 1.0 | 1.6 | 50 | 3.5 | 6.3 | — | 0.50 | 0.78 | 1.6 | 12.5 |
| JRE-2-83-1 | | 4-Cl | | 177-178 | 2.0 | 6.3 | 13 | 2.0 | 3.1 | 1.6 | 0.95 | 1.6 | 3.1 | 0.55 | 0.78 | 1.6 | 12.5 |
| JRE-3-88-1 | | 3-Cl | | 128-129 | 0.20 | 0.39 | 3.1 | 0.35 | 0.78 | 1.6 | 0.95 | 1.6 | 6.3 | 0.30 | 0.78 | 0.78 | 9.0 |
| EVK-III-001 | | | | | 0.60 | 1.6 | 13 | 0.85 | 1.6 | 1.6 | 1.0 | 1.6 | | 0.45 | 0.78 | 1.6 | 6.0 |
| EVK-III-002 | | | | 228-230 | ND | ND | ND | ND | ND | ND | ND | ND | ND | ND | ND | ND | |
| JRE-4-16-1 | | | | 124-125 | 3.5 | 10 | — | 1.5 | 2.5 | 5.0 | 0.90 | 1.3 | 1.3 | 1.5 | 5.0 | 5.0 | 8.3 |
| JRE-2-89-1 | | | | 182-183 | 15 | 50 | — | 4.0 | 6.3 | 13 | 10 | 50 | — | 1.5 | 3.1 | 13 | >25 |
| EVK-II-091 | | | | | 0.80 | 1.3 | — | 0.45 | 0.63 | 5.0 | 0.50 | 1.3 | 5.0 | 0.45 | 0.63 | 2.5 | >10 |
| Amph B | | | | | 0.25 | 0.63 | 1.3 | 0.85 | 2.5 | 2.5 | 0.90 | 2.5 | 2.5 | ND | | | 6.5 |

Abbreviations: Ca = *Candida albicans*; Cn = *Cryptococcus neoformans*; Af = *Aspergillus fumigatus*; Amph B = Amphotericin B; NA = Not active at 20 μg/mL; Cp = Cyclohexypentyl; (-) = >20 μg/mL; ND = Not determined

[c]Recrystallization solvents are A = MeOH, B = MeOH-CH₂Cl₂, C = MeOH-Et₂O, D = MeOH-EtOAc

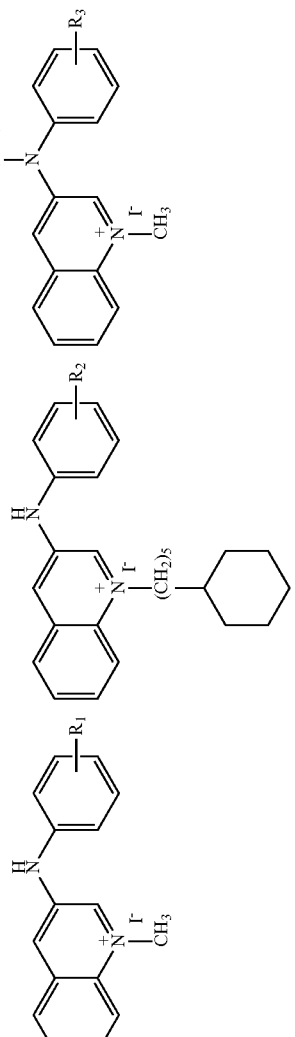

TABLE 2-continued

Physicochemical Data and Antifungal/Anti-MRSA Activities (in μg/mL) of Synthetic Compounds

| Comp | R₁ | R₂ | R₃ | MP °C(e) | Ca IC₅₀ | Ca MIC | Ca MFC | Cn IC₅₀ | Cn MIC | Cn MFC | A fu IC₅₀ | A fu MIC | A fu MFC | MRSA IC₅₀ | MRSA MIC | MRSA MFC | TC₅₀ Vero Cells |
|---|---|---|---|---|---|---|---|---|---|---|---|---|---|---|---|---|---|

EVK-III-001

EVK-III-002

JRE-4-13-1

TABLE 3

Physicochemical Data and Antifungal/Anti-MRSA Activities (in μg/mL) of Synthetic Compounds Structure E: β-carboline with N⁺—(CH₂)₅C₆H₁₁ and I⁻ counterion (positions 1, 4, 8, 11 labeled; Rn on aromatic ring; NH at position 8)

Structure F: β-carboline with N⁺—CH₃ and I⁻ counterion; N—CH₂(CH₂)₄C₆H₁₁

| Compound[a] | Str; R$_n$ | MP (°C)[b] | Ca IC$_{50}$ | Ca MIC | Ca MFC | Cn IC$_{50}$ | Cn MIC | Cn MFC | A fu IC$_{50}$ | A fu MIC | A fu MFC | MRSA IC$_{50}$ | MRSA MIC | MRSA MFC | TC$_{50}$ Vero Cells |
|---|---|---|---|---|---|---|---|---|---|---|---|---|---|---|---|
| JRE-3-4-1 | E; 10CF₃ | 210-212 | 2.0 | 6.3 | 13 | 9.0 | — | — | 10 | — | — | 1.0 | 1.6 | 3.1 | 10.5 |
| JRE-3-10-1 | E; 9-Cl | 223-225 | >20 | — | — | >20 | — | — | >20 | — | — | 5.0 | 25 | — | 9.3 |
| JRE-3-100-1 | F; H | 249-251 | 0.80 | 2.5 | 10 | 1.5 | 2.5 | 5.0 | 3.5 | 5.0 | 10 | 0.70 | 1.3 | 1.3 | >10 |
| JRE-3-84-1 | F; 9-Cl | 266-268 | 0.70 | 1.3 | 2.5 | 0.80 | 1.3 | 2.5 | 1.5 | 2.5 | 5.0 | 0.80 | 1.3 | 1.3 | >10 |
| JRE-3-13-1 | F; 10-Cl | 246-248 | 0.90 | 1.6 | 1.6 | 0.90 | 1.6 | 1.6 | 2.0 | 6.3 | 25 | 0.50 | 0.80 | 0.80 | >10 |
| JRE-5-31-1 | F; 9-CF₃ | 238-240 | 0.80 | 1.3 | — | 0.85 | 1.3 | 2.5 | 1.5 | 5.0 | 10 | 0.70 | 1.3 | 1.3 | >10 |
| JRE-4-17-1 | F; 10-CF₃ | 231-233 | 3.5 | 5.0 | 10 | 3.0 | 5.0 | 5.0 | 3.5 | 10 | 10 | 1.5 | 2.5 | 5.0 | >10 |
| JRE-4-46-1 | F; 9-OMe | 215-217 | ND | | | ND | | | ND | | | ND | | | ND |
| JRE-4-24-1 | F; CO₂-Isop | 242-243 | ND | | | ND | | | ND | | | ND | | | >10 |
| Cipro | | | | | | | | | | | | 0.09 | 0.5 | >20 | >10 |
| Amph B | | | 0.25 | 0.63 | 1.3 | 0.85 | 2.5 | 2.5 | 0.90 | 2.5 | 2.5 | ND | | | 6.5 |

Abbreviations: Ca = *Candida albicans*; Cn = *Cryptococcus neoformans*; Af = *Aspergillus fumigatus*; Amph B = Amphotericin B; NA = Not active at 20 μg/mL; Cp = Cyclohexypentyl; (-) = >20 μg/mL; ND = Not determined
[a]All compounds were subjected to CHN analysis and each passed within 0.4% of the theoretical value.
[b]Melting points were uncorrected.

The quinolinium compound of the present invention may be used in the manufacture of a drug product that is useful for the treatment of bacterial, fungal and protozoan infections in animal and human subjects.

The invention is further described in connection with the following non-limiting examples.

EXAMPLE 1

Synthesis of 3-(2-Trifluoromethyl-phenylsulfanyl)quinolinium salt

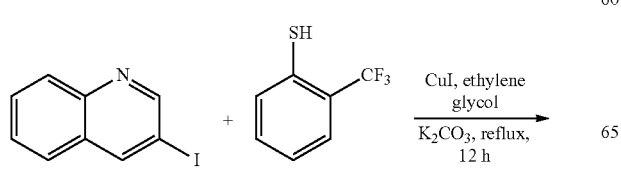

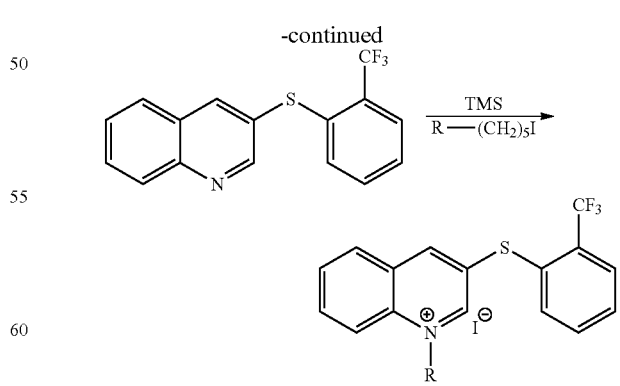

R = (CH₂)₅C₆H₅ or (CH₂)₅C₆H₁₁

A mixture of 3-iodoquinoline (6 g, 23.5 mmol), 2-trifluoromethyl benzenethiol (5 g, 28 mmol), CuI (225 mg, 3.89 mmol), ethylene glycol (3.5 g, 56.4 mmol), K$_2$CO$_3$ (8 g, 58 mmol) in isopropanol (20 mL) was refluxed under N$_2$ for 12 h. The reaction mixture was filtered through a short pad of silica gel and the filtrate was concentrated in vacuo to dryness. The product was purified by flash column chromatography on silica gel to give the product 3-(2-trifluoromethyl-phenylsulfanyl)-quinoline (8.1 g, 95%)

A mixture of 3-(2-trifluoromethyl-phenylsulfanyl)-quinoline (370 mg, 1.21 mmol), (5-iodo-pentyl)-benzene (520 mg, 1.9 mmol) in tetramethylene sulfone (1 mL) was sealed in a tube and heated at 100° C. for 12 h. Ether (10 mL) was added resulting in a solid product. The product was crystallized from MeOH-Et$_2$O to yield 1-(5-phenyl-pentyl)-3-(2-trifluoromethyl-phenylsulfanyl)-quinolinium iodide (632 mg, 90%). Mp 227-229° C.

$^1$H NMR (DMSO), 9.72 (1H, s), 9.24 (1H, s), 8.60 (1H, d, J=8.7 Hz), 8.42 (1H, d, J=7.8 Hz), 8.27 (1H, dd, J=3.9, 8.1 Hz), 8.04 (1H, dd, J=7.2, 7.8 Hz), 7.92 (1H, d, J=5.7 Hz), 7.61 (3H, m), 7.22 (2H, m), 7.13 (3H, m), 5.04 (2H, br s), 2.54 (2H, t, J=6.6 Hz), 1.98 (2H, br s), 1.60 92H, br s), 1.37 (2H, br s).

EXAMPLE 2

Part A

Step 1: Synthesis of [Ph$_3$Bi(OAc)$_2$]

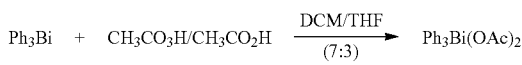

To a solution of Ph$_3$Bi (5 g, 11.3 mmol) in 30 ml of CH$_2$Cl$_2$/THF (7:3) at 0° C., was added drop wise CH$_3$CO$_3$H (2.9 ml of a 32% solution in CH$_3$COOH, 1.2 eq). The mixture was stirred at room temperature for 1 hr. Diethyl ether (30 ml) was added and the resulting precipitate was filtered, washed with Et$_2$O, collected and dried, (5.7 g).

Mp: 192-194° C.
$^1$H NMR (CDCl$_3$): δ 1.82 (s, 6H), 7.45-7.60 (m, 9H), 8.15 (d, J=8.1 Hz, 6H).

Step 2: Synthesis of Phenyl-quinolin-3-yl-amine

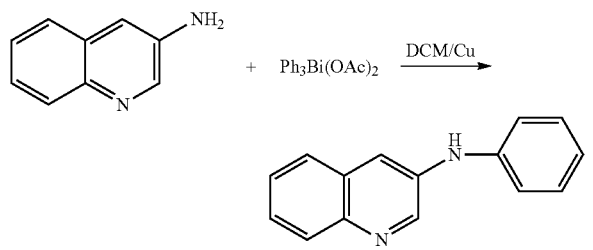

A mixture of 3-aminoquinoline (800 mg, mmol) in 30 ml of CH$_2$Cl$_2$, Cu powder (272 mg,) and triphenylbismuth diacetate (4.64 gm) was stirred at room temperature overnight. The crude reaction mixture was diluted with CH$_2$Cl$_2$ (20 ml) and filtered, the filtrate was washed with H$_2$O followed by brine. The organic phase was dried over anhydrous Na$_2$SO$_4$ solvent was removed under reduced pressure and the crude product was purified by column chromatography using EtOAc and hexane (1:9) as eluent. The pure product was a pale greenish solid (800 mg).

$^1$H NMR (CDCl$_3$): δ 6.0 (brs, NH), 7.05 (t, 1H, J=7.2 Hz), 7.15 (d, 2H, J=8.10 Hz), 7.35 (t, 2H, J=8.4 Hz), 7.45-7.55 (m, 2H), 7.60 (dd, 1H, J=1.8, 7.5 Hz), 7.70 (d, 1H, J=2.7 Hz), 8.00 (d, 1H, J=7.8 Hz), 8.70 (d, 1H, J=2.7 Hz).

Step 3: Synthesis of (5-Bromo-pentyl)-cyclohexane

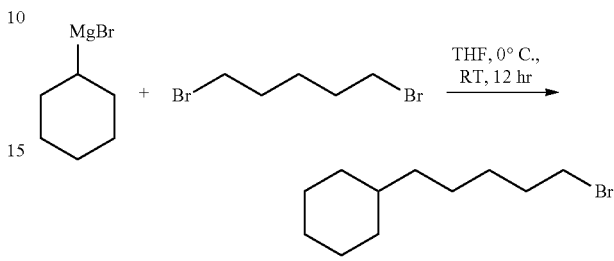

To a solution of 1,5-dibromopentane (16 gm, 69.97 mmol) in THF (20 ml) was added a solution of (Li$_2$CuCl$_4$ in ether, 14 ml) under nitrogen at 5-10° C. and stirred for 25 minutes. Cyclohexyl magnesium bromide (10 gm, 69.97 mmol) was added dropwise with stirring for about 30 minutes. The reaction mixture was stirred at 0° C. for another 1 h and stirred at room temperature for 12 hr. The reaction mixture was cooled to 0° C. in ice, saturated NH$_4$Cl solution (20 ml) was added and the resulting mixture was extracted with EtOAc (4×25 ml). The organic layer was separated, washed with brine and dried over anhydrous Na$_2$SO$_4$. The solvent was removed under reduced pressure and the crude product was purified by column chromatography using hexane as an eluent. The pure product was an oily liquid (12.84 gm).

$^1$H NMR (CDCl$_3$): 0.8 (t, 2H, J=10.2 Hz), 1.00-1.38 (m, 9H), 1.52-168 (m, 6H), 1.70-1.80 (m, 2H), 3.38 (t, 2H, J=7.2 Hz).

Step 4: Synthesis of (5-Iodo-pentyl)-cyclohexane

A mixture of (5-bromopentyl)cyclohexane (2 gm, 8.6 mmol) in acetone (20 ml), and sodium iodide (2.57 g, 17.1533 mmol) was heated for 60° C. for 12 hrs. The mixture was allowed to cool to room temperature and the solvent was evaporated. The residue was diluted with EtOAc (30 ml), H$_2$O (20 ml) was added, separated and the organic phase was washed with brine (30 ml). The organic layer was dried over anhydrous Na$_2$SO$_4$; solvent was evaporated under reduced pressure and the crude product was purified by column chromatography using hexane as eluent. The pure product was an oily liquid (1.36 gm).

$^1$H NMR (CDCl$_3$): δ 0.8 (t, 2H, J=10.2 Hz), 1.00-1.38 (m, 9H), 1.52-168 (m, 6H), 1.70-1.80 (m, 2H), 3.10 (t, 2H, J=6.9 Hz).

Step 5: Synthesis of
1-(5-Cyclohexyl-pentyl)-3-phenyl-quinolinium iodide

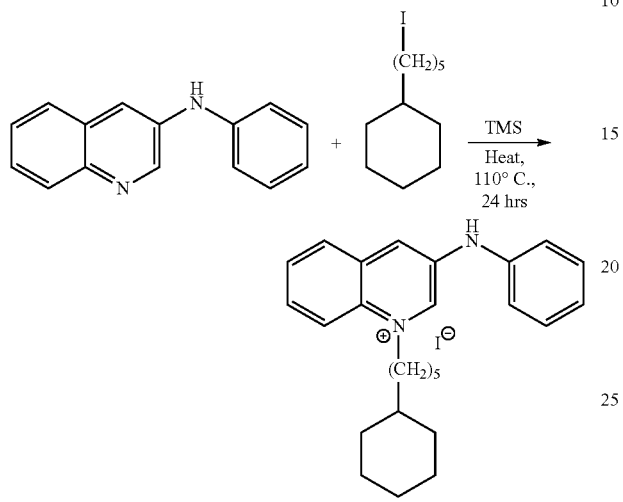

A mixture of phenyl-quinolin-3-yl-amine (100 mg, 0.4539 mmol) in toluene (3 ml) and 5-iodopentylcyclohexane (636 mg, 2.3 mmol) in a sealed pressure tube was stirred at 110° C. for 24 hours. The reaction mixture was allowed to cool to room temperature, diluted with Et$_2$O (15 ml) and the resulting precipitate was filtered and washed with Et$_2$O (3×20 ml). The crude product was purified by column chromatography using MeOH/Et$_2$O as eluent. The pure product was an orange solid (65 mg). Mp: 156-158° C.).

$^1$H NMR (CD$_3$OD): δ 0.80-1.00 (m, 2H), 1.00-1.38 (m, 7H), 1.40-1.58 (m, 4H), 1.60-1.80 (m, 4H), 2.00-2.20 (m, 2H), 5.00 (t, 2H, J=7.2 Hz), 7.20 (t, 1H, J=6.8 Hz), 7.35 (d, 2H, J=8.6 Hz), 7.46 (t, 2H, J=7.0 Hz), 7.80 (t, 1H, J=7.6 Hz), 7.82-8.00 (m, 1H), 8.10 (d, 1H, J=8.4 Hz), 8.38 (d, 1H, J=9.0 Hz), 8.45 (d, 1H, J=2.4 Hz), 9.0 (d, 1H, J=2.7 Hz). Anal Calcd for: C$_{26}$H$_{33}$IN$_2$.1.4 H$_2$O: C, 56.69; H, 6.55; N, 5.08. Found: C, 56.73; H, 6.26; N, 4.93.

Step 6: Synthesis of (5-Iodopentyl)benzene

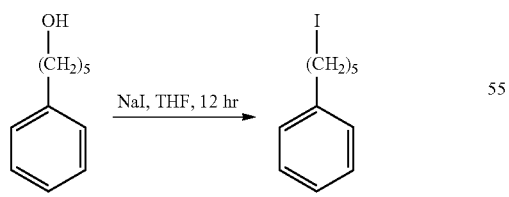

A mixture of 5-phenyl-pentane-1-ol (1.0 gm, 6.09 mmol) in CH$_2$Cl$_2$ (20 ml), triphenyl phosphine (2.35 gm, 8.52 mmol), imidazole (0.58 gm, 8.52 mmol) and elemental iodine (2.16 gm, 8.52 mmol) was stirred at room temperature for 12 h. The solvent was evaporated under reduced pressure. The residue was diluted with EtOAc (30 ml), H$_2$O (20 ml) was added, separated and the organic phase was washed with brine (30 ml). The organic layer was dried over anhydrous Na$_2$SO$_4$; solvent was evaporated under reduced pressure and the crude product was purified by column chromatography using hexane as eluent. The crude product was purified by column chromatography using hexane as eluent. The pure product was an oily liquid (750 mg).

$^1$H NMR (CDCl$_3$): δ 1.30-1.70 (m, 4H), 1.80 (m, 2H), 2.6 (t, 2H, J=7.2 Hz), 3.10 (t, 2H, J=7.8 Hz), 7.00-7.34 (m, 5H).

Step 7: Synthesis of
1-(5-cyclohexyl-pentyl)-3-phenylquinolinium iodide

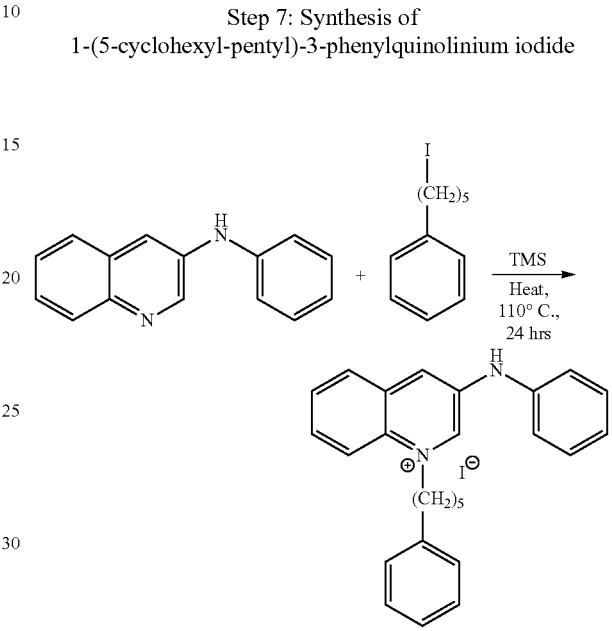

A mixture of phenylquinolin-3-yl-amine (100 mg, 0.46 mmol) in toluene (2 ml) and 5-iodopentylbenzene (373 mg, 1.36 mmol) in sealed pressure tube was stirred at 110° C. for 24 hours. The reaction mixture was allowed to cool to room temperature, diluted with Et$_2$O (15 ml), and the resulting precipitate was filtered and washed with Et$_2$O (3×20 ml). The crude product was purified by column chromatography using MeOH/Et$_2$O as eluent. The pure product was an orange solid (75 mg). Mp: 140-141° C.

$^1$H NMR (CD$_3$OD): δ 1.42-1.56 (m, 2H), 1.66-178 (m, 2H), 2.04-2.18 (m, 2H), 2.58-2.68 (t, 2H, J=7.2 Hz), 4.88-5.04 (t, 2H, J=7.8 Hz), 7.08-7.24 (m, 6H), 7.14 (dd, 2H, J=0.9, 7.5 Hz), 7.40-7.44 (t, 2H, J=8.4 Hz), 7.76-7.84 (t, 1H, J=7.5 Hz), 7.86-7.94 (m, 1H), 8.08 (d, 1H, J=8.4 Hz), 8.30 (d, 1H, J=9.0 Hz), 8.46 (d, 1H, J=2.4 Hz), 9.04 (d, 1H, J=2.7 Hz). Anal Calcd for: C2$_6$H$_{27}$IN$_2$.1H$_2$O: C, 60.92; H, 5.70; N, 5.47. Found: C, 60.79; H, 5.33; N, 6.38.

Part B

Synthesis of 3-Anilinoquinolinium salt

Scheme 2

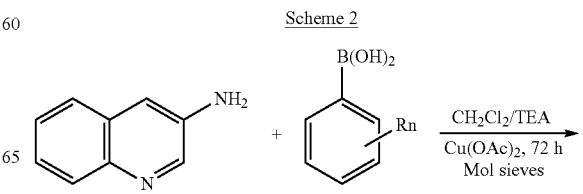

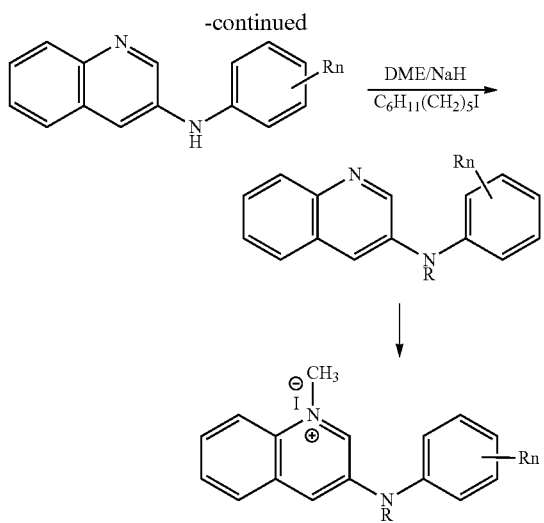

R = (CH₂)₅C₆H₁₁
Rn (Defined in Tables)

(A): General Procedure for the synthesis of phenyl-quinoline amine derivatives

To a solution of 3-amino quinoline (1 gm, mmol) in CH₂Cl₂ (30 mL) and 4-chlorophenyl boronic acid (2 gm, mmol, 1.6 eq) was added portion wise, triethylamine (1.5 gm, 1.6 eq), Cu(OAc)₂ (1.5 gm, mmol, 1.6 eq) and molecular sieves (2 gm) powder. The reaction mixture was stirred at room temperature for 12-24 hrs. The reaction was quenched with aqueous NH₃ (15 ml) and extracted with CH₂Cl₂, (3×25 ml) washed with brine solution and dried over anhydrous Na₂SO₄. The solvent was evaporated under reduced pressure and the pure product was obtained by column chromatography using EtOAc and hexane as eluent. 1H-NMR (DMSO-d₆): δ 7.24 (d, 2H, J=8.7 Hz), 7.34 (d, 2H, J=9.0 Hz), 7.46-7.52 (m, 2H), 7.78-7.82 (m, 1H), 7.84-7.90 (m, 2H), 8.68 (d, 1H, J=3.0 Hz), 9.40 (s, NH).

(B): General procedure for the synthesis of (5-Cyclohexyl-pentyl)-phenyl-quinolin-3-yl-amines A mixture of 4-(chlorophenylquinolin-3-yl-amine (100 mg), DME (5 ml), NaH (20 mg) 5-iodo-pentyl-cyclohexane (636 mg) was stirred at room temperature for 12 hours. Solvent was evaporated, the residue diluted with H₂O (10 mL), extracted with EtOAc (2×30 mL), washed with brine and dried over anhydrous Na₂SO₄. The solvent was removed under reduced pressure and the crude product was purified by column chromatography to yield the pure product as an oily liquid (70 mg). 1H-NMR: (CDCl₃): δ 8.64 (d, 1H, J=2.4 Hz), 8.00 (d, 1H, J=8.4 Hz), 7.66 (dd, 1H, J=, 8.1, 1.8 Hz), 7.58-7.44 (m, 3H), 7.26 (d, 2H, J=9.0 Hz), 7.00 (d, 2H, J=8.8 Hz), 3.70 (t, 2H, J=7.8 Hz), 1.76-1.60 (m, 7H), 1.40-1.30 (m, 5H), 1.20-1.10 (m, 5H), 0.80-0.60 (t, 2H, J=9.3 Hz).

(C): General procedure for the synthesis of-3-[(5-Cyclohexyl-pentyl)-phenyl-amino]-1-methyl-quinolinium iodides JRE-4-9-1: A mixture of [(4-chlorophenyl)-(5-cyclohexylpentyl)]-quinolin-3-yl-amine (65 mg), in toluene (3 ml) and CH₃I (0.2 mL) in a sealed pressure tube was stirred at 110° C. for 24 hours. The reaction mixture was allowed to cool to room temperature, diluted with Et₂O (15 ml) and the resulting precipitate was filtered and washed with Et₂O (20 ml) to yield the pure product as an orange solid (50 mg). Mp: 176-177. ¹H-NMR: (DMSO-d₆): δ 9.10 (d, 1H, J=2.7 Hz), 8.46 (d, 1H, J=2.4 Hz), 8.26 (d, 1H, J=8.7 Hz), 8.20-8.18 (dd, 1H, J=7.2, 1.2 Hz), 7.96-7.90 (m, 1H), 7.84 (t, 1H, J=7.8 Hz), 7.50 (d, 2H, J=9.0 Hz), 7.36 (d, 2H, J=9.0 Hz), 4.54 (s, 3H), 3.86 (t, 2H, J=7.5 Hz), 1.70-1.50 (m, 7H), 1.40-1.24 (m, 4H), 1.20-1.04 (m, 6H), 0.84-0.74 (t, 2H, J=10.2 Hz).

EXAMPLE 3

Synthesis of Indolo[2,3-c]quinolinium Iodides

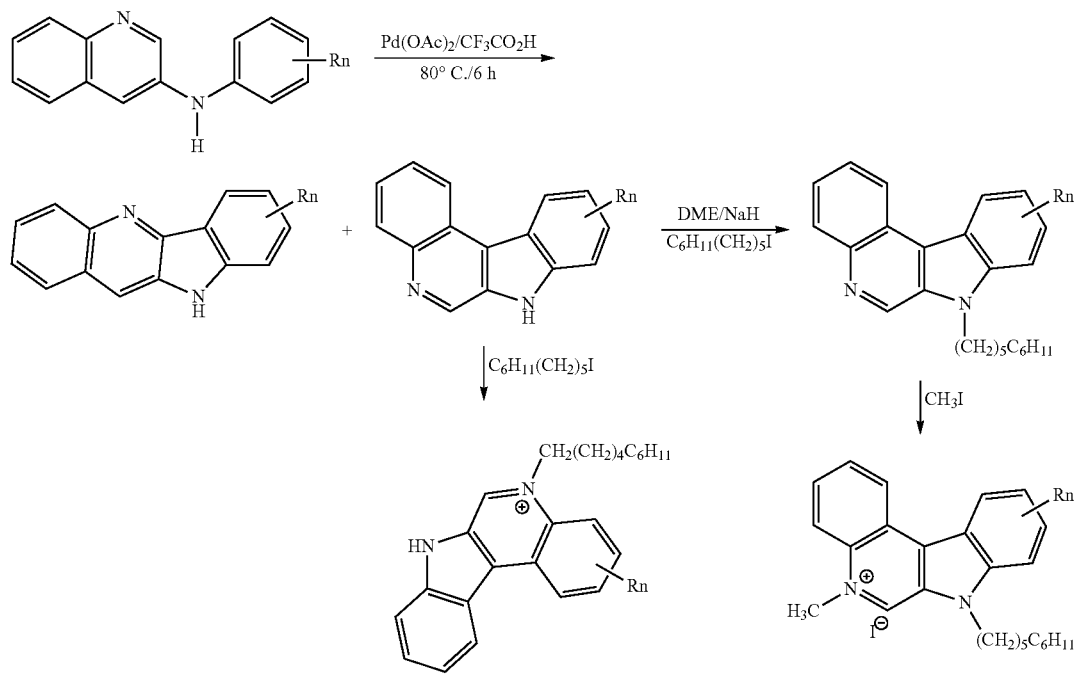

The above synthesized 3-anilinoquinoline was used as the starting material. A palladium catalyzed ring closure reaction was utilized to obtain both linear and angular quindoline ring systems, which is described by Etukala, J. R.; Suresh Kumar, E. V. K.; Ablordeppey, S. Y., *A Short and Convenient Synthesis and Evaluation of the Antiinfective Properties of Indoloquinoline Alkaloids: 10H indolo[3,2-b]quinoline and 7H-indolo[2,3-c]quinolines, J. Heterocycl Chem.*, 2008, 45, 507-511, and Fan Pingchen, et al., *An Alternativie Synthesis of the 10H-Indolo[3,2-b]quiniline and its Selective N-Alkylation, J. Heterocycl. Chem.*, 1997, 34, 1789-1794, both publications herein incorporated by reference. The ratio of linear to angular ring systems are dependent on the ring substituents. Overall, the angular systems were found to predominate in all cases except for the 9-substituted analogs.

(A): General procedure for the synthesis of 7H-indolo-[3,2-c]quinoline analogs

A mixture of 4-(chlorophenylquinolin-3-yl-amine (400 mg), $CF_3COOH$ (8 ml), $Pd(OAc)_2$ (300 mg) was refluxed for 6 hr at 80° C. The reaction mixture was allowed to cool to room temperature, poured in ice cold water (15 ml), neutralized with aqueous ammonia and extracted with EtOAc (3×50 mL), washed with brine and dried over anhydrous $Na_2SO_4$. The solvent was removed under reduced pressure and the crude product was purified by column chromatography to yield the pure solid product (130 mg). Mp: 146-148° C. 1H-NMR: (DMSO-$d_6$): δ 9.52 (s, 1H), 8.96 (d, 1H, J=8.1 Hz), 8.86 (d, 1H, J=1.5 Hz), 8.24 (d, 1H, J=8.1 Hz), 7.88-7.78 (m, 3H), 7.70-7.66 (dd, 1H, J=6.6, 2.1 Hz).

(B): General procedure for the synthesis of 7-(5-Cyclohexyl-pentyl)-7H-indolo quinolines A mixture of 10-chloro-7H-indolo[2,3-c]-quinoline (120 mg), DME (5 ml), NaH (30 mg) and 5-iodo-pentyl-cyclohexane (636 mg) was stirred at room temperature for 12 h, solvent was evaporated and the residue diluted with $H_2O$ (10 mL). The resulting mixture was extracted with EtOAc (2×30 mL), washed with brine and dried over anhydrous $Na_2SO_4$. The solvent was removed under reduced pressure and the crude product was purified on column chromatography to yield the pure solid product (70 mg).
1H NMR: ($CDCl_3$): δ 9.26 (s, 1H), 8.62 (d, 1H, J=8.4 Hz), 8.54 (d, 1H, J=1.2 Hz), 8.32 (d, 1H, J=8.4 Hz), 7.74 (t, 1H, J=7.2 Hz), 7.70 (t, 1H, J=8.1 Hz), 7.60-7.52 (m, 2H), 4.52 (t, 2H, J=7.2 Hz), 1.94 (t, 2H, J=6.9 Hz), 1.70-1.50 (m, 5H), 1.40-1.30 (m, 4H), 1.20-1.00 (m, 6H), 0.86-0.76 (t, 2H, J=10.8 Hz).

EXAMPLE 4

General procedure for the synthesis of 10-substituted-7-(5-cyclohexyl-pentyl)-5-methyl-7H-indolo[2,3-c]quinolin-5-ium iodide (A): 10-Chloro-7-(5-cyclohexyl-pentyl)-5-methyl-7H-indolo[2,3-c]quinolin-5-ium iodide A mixture of 10-chloro-7-(5-cyclohexyl-pentyl)-7H-indolo[2,3-c]-quinoline (65 mg) in toluene (3 ml) and $CH_3I$ (0.3 mL) was stirred in a sealed pressure tube at 110° C. for 24 hours. The reaction mixture was allowed to cool to room temperature, diluted with $Et_2O$ (15 ml) and the resulting precipitate was filtered and washed with $Et_2O$ (3×20 ml) to yield the pure angular product as an orange solid (50 mg). Mp 246-248° C.

1H-NMR: (DMSO-$d_6$): δ 10.28 (s, 1H), 9.26-9.20 (m, 1H), 9.06 (d, 1H, J=1.5 Hz), 8.58-8.54 (m, 1H), 8.14 (d, 1H, J=9.0 Hz), 8.10-8.06 (m, 2H), 7.94-7.90 (dd, 1H, J=7.5, 1.8 Hz), 4.76-4.70 (m, 5H), 1.90-1.80 (t, 2H, J=6.6 Hz), 1.64-1.50 (m, 5H), 1.34-1.20 (m, 4H), 1.16-1.00 (m, 6H), 0.80-0.72 (t, 2H, J=9.9 Hz).

(B): 10-Trifluoromethyl-7-(5-cyclohexyl-pentyl)-5-methyl-7H-indolo[2,3-c]quinolin-5-ium iodide Mp: 231-233° C.
1H-NMR: (DMSO-$d_6$): δ 10.34 (s, 1H), 9.40-9.32 (m, 1H), 9.30 (s, 1H), 8.64-8.58 (m, 1H), 8.30 (d, 1H, J=9.0 Hz), 8.20-8.10 (m, 3H), 4.80-4.70 (m, 5H), 1.94-1.86 (t, 2H, J=7.2 Hz), 1.64-1.50 (m, 5H), 1.40-1.26 (m, 4H), 1.10-1.00 (m, 6H), 0.80-0.74 (t, 2H, J=10.2 Hz).

It must be emphasized that the law does not require and it is economically prohibitive to illustrate and teach every possible embodiment of the present claims. Hence, the above-described embodiments are merely exemplary illustrations of implementations set forth for a clear understanding of the principles of the invention. Many variations and modifications may be made to the above-described embodiments without departing from the scope of the claims. All such modifications, combinations, and variations are included herein by the scope of this disclosure and the following claims.

The invention claimed is:

1. A compound having the formula (I):

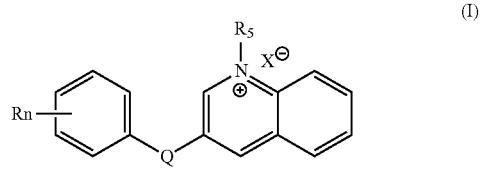

or a pharmaceutically acceptable salt thereof, wherein:
Rn is an electron withdrawing or electron donating group, and n is the position of substitution of R;
$R_5$ is $(CH_2)_5$—$C_6H_5$ or $(CH_2)_5$—$C_6H_{11}$;
Q is NH, N—$CH_3$, N—$R_5$, S, SO or O; and
$X^-$ is a pharmaceutically acceptable counterion.

2. A compound of claim 1, wherein $R_n$ is an electron withdrawing or electron donating group selected from the group consisting of H, halogen, —$CF_3$, O—$R_1$, S—$R_1$, S—$R_1$—O, S—$R_1O_2$, CN, $NO_2$, and $NR_1R_2$, wherein $R_1$ and $R_2$ may be the same or different and are alkyl or hydrocarbylaryl.

3. A compound of claim 2, wherein said halogen is Br, Cl, F or I.

4. A compound of claim 1, wherein the counterion is iodide, bromide, chloride, nitrate, tosylate or triflate.

5. A pharmaceutical composition comprising a pharmacologically effective amount of a compound in accordance with claim 1, in combination with a pharmaceutically acceptable carrier.

6. A pharmaceutical composition produced by combining a compound in accordance with claim 1 with a pharmaceutically acceptable carrier.

7. An article of manufacture comprising packaging material and a pharmaceutical agent contained within said packaging material, wherein said pharmaceutical agent is effective for the treatment of a subject suffering from one or more pathological conditions, and wherein said packaging material comprises a label which indicates that said pharmaceutical agent can be used for ameliorating the symptoms associated with conditions and wherein said pharmaceutical agent is a compound of claim 1.

* * * * *

UNITED STATES PATENT AND TRADEMARK OFFICE
CERTIFICATE OF CORRECTION

PATENT NO.        : 8,288,410 B2
APPLICATION NO.   : 12/169165
DATED             : October 16, 2012
INVENTOR(S)       : Seth Y. Ablordeppey It is certified that error appears in the above-identified patent and that said Letters Patent is hereby corrected as shown below:

In the Specification

Column 1, Line 7, should read as follows

This invention was made with government support under NIH/NCRR/RCMI G12RR03020, and NIH/NCRR/HHSI C06 RR012512-01 awarded by the National Institutes of Health. The government has certain rights in the invention.

Signed and Sealed this
Third Day of November, 2015

Michelle K. Lee
*Director of the United States Patent and Trademark Office*